United States Patent [19]

Sommadossi et al.

[11] Patent Number: 5,077,280
[45] Date of Patent: Dec. 31, 1991

[54] TREATMENT OF VIRAL INFECTIONS

[75] Inventors: Jean-Pierre Sommadossi, Birmingham, Ala.; Mahmoud H. el Kouni, Providence, R.I.

[73] Assignee: Brown University Research Foundation, Providence, R.I.

[21] Appl. No.: 180,525

[22] Filed: Apr. 12, 1988

[51] Int. Cl.$^5$ .............................................. A61K 31/70
[52] U.S. Cl. ........................................ 514/49; 424/10; 514/50; 514/51; 514/274; 514/814; 514/922
[58] Field of Search .................. 514/49, 50, 51, 274, 514/814, 922; 424/10

[56] References Cited

U.S. PATENT DOCUMENTS

| | | | |
|---|---|---|---|
| 3,282,921 | 11/1966 | Verheyden et al. | 260/211.5 |
| 3,687,931 | 8/1972 | Verheyden et al. | 260/211.5 |
| 3,755,295 | 8/1973 | Verheyden et al. | 260/211.5 |
| 3,775,397 | 11/1973 | Etzold et al. | 260/211.5 |
| 3,817,982 | 6/1974 | Verheyden et al. | 260/211.5 |
| 4,071,680 | 1/1978 | Cook | 536/23 |
| 4,093,715 | 6/1978 | Lin et al. | 424/180 |
| 4,128,639 | 12/1978 | Lin et al. | 424/180 |
| 4,210,638 | 7/1980 | Greer | 424/180 |
| 4,230,698 | 10/1980 | Bobek et al. | 424/180 |
| 4,331,662 | 5/1982 | Eckstein et al. | 424/180 |
| 4,604,382 | 8/1986 | Lin et al. | 514/49 |
| 4,613,604 | 9/1986 | Chu et al. | 514/274 |
| 4,681,933 | 7/1987 | Chu et al. | 536/23 |
| 4,780,453 | 10/1988 | Rideout et al. | 514/50 |
| 4,950,466 | 8/1990 | Calabresi et al. | 514/258 |

FOREIGN PATENT DOCUMENTS

| | | |
|---|---|---|
| 217580 | 4/1987 | European Pat. Off. . |
| 286425 | 10/1988 | European Pat. Off. . |
| 287215 | 10/1988 | European Pat. Off. . |
| 2027782 | 8/1975 | Japan ................................. 536/23 |

OTHER PUBLICATIONS

Balzarini et al., Biochemical and Biophysical Research Communications, vol. 140, No. 2, pp. 735-742, Oct. 30, 1986.
3'-Substituted 2',3'-Dideoxynucleoside Analogues as Potential Anti-HIV CHTLV-III/LAV) Agents, Herdewijn et al., J. Med. Chem. 30, 1270-1278.
Horwitz et al., "Nucleosides V. The Monomesylates . . . " vol. 29, *The Rollin H. Stevens Memorial Library* (1964), p. 2076.
Lin et al., "Synthesis and Biological Activity of Several Amino Analogues of Thymidine", vol. 21, No. 1, Journal of Medicinal Chemistry, pp. 109-112 (1977).
Niedzwicki et al., "Pyrimidine Acyclonucleosides . . . ", vol. 30, No. 15, *Biochemical Pharmacology*, pp. 2097-2101, (1981).
Lin et al., "Synthesis of . . . New Potent Uridine Phosphorylase Inhibitors with High Water Solubility", vol. 28, No. 971, *Journal of Medicinal Chemistry* (1985).
Sommadossi et al., "Toxicity of 3'-Azido-3'-Deoxythymidine and . . . ", *Antimicrobial Agents and Chemotherapy*, Mar. 1978, pp. 452-454.
Lin et al., "Antiviral Activity of 2',3'-Dideoxycytidin . . . ", vol. 36, No. 3, *Biochemical Pharmacology*, pp. 311-316, (1987).
Mitsuya et al., "3'-Azido-3'-Deoxythymidine (BW A 509U): . . . ", vol. 82, *Proc. Natl. Acad. Sci.*, U.S.A., pp. 7096-7100 (1985).
Schinazi et al., "Selective In Vitro Inhibition of Human Immunodeficiency Virus . . . ", Abbott-UCLA Symposium, Apr. 1-6, 1987.
Ghazzouli et al., Paragraph from Antiviral Research, vol. 9, No. 1, Jan./Feb. 1988.
Niedzwicki et al., "5 α Benzylacyclouridine and 5-Benzyloxybenzylacyclouridine . . . ", vol. 31, No. 10, *Biochemical Pharmacology*, 1982, pp. 1857-1861.
Park et al., "Inhibition of Uridine Phosphorylase . . . ", vol. 35, No. 21, *Biochemical Pharmacology*, pp. 3853-3855 (1986).
Siegel et al., "Biological Activity of Two Novel Inhibitors . . . ", vol. 34, No. 7, *Biochemical Pharmacology*, pp. 1121-1124 (1985).
Darnowski et al., "Tissue-Specific Enhancement of Uridine Utilization . . . ", vol. 45, *Cancer Research*, pp. 5364-5368 (1985).
Monks et al., "Effect of 5-Benzylacyclouridine . . . by the Isolated Rat Liver", vol. 32, No. 13, *Biochemical Pharmacology*, pp. 2003-2009 (1983).
Chu et al., "Potentiation of 5-Fluoro-2'-Deoxyuridine Antineoplastic Activity . . . ", vol. 44, *Cancer Research*, pp. 1852-1856 (1984).
Lee et al., "Inhibition of Nucleoside Transport in Murine Lymphoma . . . ", vol. 44, *Cancer Research*, pp. 3744-3748 (1984).
Naguib et al., "New Analogues of Benzylacyclouridines . . . ", vol. 36, No. 13, *Biochemical Pharmacology*, pp. 2195-2201 (1987).
Falcone et al., "Effect of Benzylacyclouridine on 3'-Azido-3'-Deoxythymidine-Induced Anemia", vol. 36, No. 3, *Clinical Research*, p. 409A (1988).
Sommadossi et al., "Enhancement of the Anti-HIV Activity . . . ", Abstracts of the 1987 ICAAC, p. 163, No. 383.
el Kouni et al., "Uridine Phosphorylase . . . ", vol. 263, *J. Biol. Chem.*, pp. 6081-6086 (1988).

*Primary Examiner*—John W. Rollins
*Assistant Examiner*—James O. Wilson
*Attorney, Agent, or Firm*—Thomas J. Engellenner; Ralph A. Loren; William C. Geary, III

[57] ABSTRACT

Treatments for viral infections are disclosed based on the finding that uridine can selectively protect and/or rescue uninfected cells, particularly human bone marrow progenitor cells, from the toxicity of pyrimidine nucleoside analogues during the treatment of retroviral diseases, such as AIDS, and that uridine phophorylase inhibitors are particularly effective in maintaining the necessary levels of uridine within such cells. A treatment for AIDS-type diseases is disclosed in which a pyrimidine nucleoside analogue and a uridine phosphorylase inhibitor are co-administered either simultaneously or sequentially to treat the viral infections and protect or rescue uninfected cells in the afflicted subject. This combination therapy also can be supplemented by direct administration of uridine.

26 Claims, No Drawings

TREATMENT OF VIRAL INFECTIONS

BACKGROUND OF THE INVENTION

The U.S. Government has rights in this invention pursuant to NIH Grants No AI 25784 and No. AI 22219.

The technical field of this invention is the treatment of infections viral diseases and, in particular, the treatment of acquired immune deficiency syndrome (AIDS) and related illnesses.

Acquired immune deficiency syndrome is generally accepted to be the result of infection with a type of retrovirus termed the human immunodeficiency virus (HIV) A number of strains or classes of HIVs have recently been identified and it also appears that HIVs are part of a broader family of retroviruses having similar genomes that are responsible for a wide range of diseases having diverse clinical manifestations.

In cases of AIDS, the infections are characterized by a marked depression in the hematological profile of the host and a general loss of the host immune response to invading pathogens, leaving the afflicted individuals extremely vunerable to opportunistic infections by other microbes. In early stages of the infection, a number of less life-threatening manifestations have been reported and are generally referred to as AIDS-related complexes.

At present, management of patients with HIV infections typically involves the administration of a pyrimidine nucleoside analogue, such as, for example, azidothymdine (3'-azido-3'-deoxythmidine or "AZT"). Such chemotherapeutic agents function by inhibiting the reverse transcriptase of the HIV and reducing the cytopathic effects of the virus.

However, the administration of AZT or related agents can have severe side effects A common complication of AZT therapy is the suppression of bone marrow cell growth in the patient (specifically granulocyte-macrophages and erythrocytes). This complication often limits the dosage or duration of therapy that can be implemented.

There exists an immediate need for therapies that can reduce the toxicity of pyrimidine nucleoside analogues when used as antiviral agents. In particular, pharmacological agents which can selectively rescue or otherwise protect uninfected cells, such as human hematopoietic progenitor cells, from the toxicity of AZT and related drugs, or otherwise permit higher doses or long term treatment protocols with such drugs, would satisfy a critical need in combatting the present AIDS epidemic.

SUMMARY OF THE INVENTION

It has been discovered that uridine can selectively protect and/or rescue uninfected cells, particularly human bone marrow progenitor cells, from the toxicity of pyrimidine nucleoside analogues during the treatment of retroviral diseases, such as AIDS, and that uridine phophorylase inhibitors are particularly effective in maintaining the necessary levels of uridine within such cells.

In one aspect of the invention, a treatment for AIDS-type diseases is disclosed in which a pyrimidine nucleoside compound, such as AZT, and a uridine phosphorylase inhibitor are co-administered either simultaneously or sequentially to treat the viral infection and protect or rescue uninfected cells in the afflicted subject, which can be either human or animal.

In another aspect of the invention, the combination therapy disclosed herein can be supplemented by direct administration of uridine. Although uridine is normally cleared rapidly by the body, the uridine phosphorylase inhibitors suppress uridine degradation in the liver. Thus, low doses of uridine can be used to "boost" plasma uridine levels and this protective uridine level can be maintained by administration of the phosphorylase inhibitors.

DETAILED DESCRIPTION

Pyrimidine nucleoside analogues useful in the present invention include, for example, 3'-azido-3'deoxythymidine (AZT);
3'-azido-2',3'-dideoxyuridine (AZddU or CS-87);
2',3'-dideoxycytidin-2'-ene (d$_4$C);
3'-deoxy-3'-deoxythymidin-2'-ene (d$_4$T); and other related compounds.

For further disclosures of pyrimidine nucleoside analogues having antiviral properties and methods of synthesizing such compounds, see U.S. Pat. No. 3,282,921 issued to Verheyden et al. on Nov. 1, 1966; U.S. Pat. No. 3,687,931 issued to Verheyden et al. on Aug. 29, 1972; U.S. Pat. No. 3,755,295 issued to Verheyden et al. on Aug. 28, 1973; U.S. Pat. No. 3,775,397 issued to Etzold et al. on Nov. 27, 1973; U.S. Pat. No. 3,817,982 issued to 071,680 issued to Cook on Jan. 31, 1978; U.S. Pat. No. 4,093,715 issued to Lin et al. on June 6, 1978; U.S. Pat. No. 4,128,639 issued to Lin et al. on Dec. 5, 1978; U.S. Pat. No. 4,210,638 issued to Greer on July 1, 1980; U.S. Pat. No. 4,230,698 issued to Bobek et al. on Oct. 28, 1980; U.S. Pat. No. 4,331,662 issued to Eckstein et al. on May 25, 1982; U.S. Pat. No. 4,604,382 issued to Lin et al. on Aug. 5, 1986; U.S. Pat. No. 4,681,933 issued to Chu et al. on July 21, 1987; Horwitz, Vol. 29 *J. Org. Chem.* pp. 2076–2078 (1964); Lin et al., Vol. 21 *J. Med. Chem.* pp. 109–112 (1978); Lin et al., Vol 36 *Biochem. Pharmacol.* pp 311–316 (1987); and Schinazi et al. *Interscience Conference on Antimicrobial Agents and Chemotheraopy* Abstract #369 (1987), herein incorporated by reference.

Uridine phosphorylase inhibitors useful in the present invention include acyclouridine compounds generally in particular, including for example, benzylacyclouridine (BAU);
benzyloxybenzylacyclouridine (BBAU);
aminomethyl-benzylacyclouridine (AMBAU);
aminomethyl-benzyloxybenzylacyclouridine (AMBBAU);
hydroxymethyl-bnezylacyclouridine (HMBAU); and
hydroxymethyl-benzyloxybenzylacyclouridine (HMBBAU).

Table I below provides a further recitation of benzylacyclouridine compounds:

TABLE I

Chemical Structures of Various Benzylacyclouridines

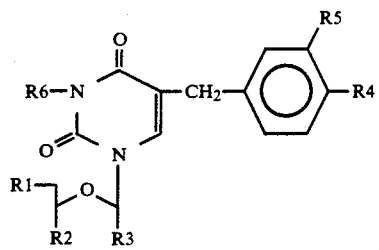

| Compound | R1 | R2 | R3 | R4 | R5 | R6 |
|---|---|---|---|---|---|---|
| BAU | —OH | —H | —H | —H | —H | —H |
| succ-BAU | —OCOCH$_2$CH$_2$COOH | —H | —H | —H | —H | —H |
| BAU-P | —OPO$_3$H$_2$ | —H | —H | —H | —H | —H |
| HM-BAU | —OH | —CH$_2$OH | —H | —H | —H | —H |
| AM-BAU | —OH | —CH$_2$NH$_2$ | —H | —H | —H | —H |
| DA-BAU | —NH$_2$ | —CH$_2$NH$_2$ | —H | —H | —H | —H |
| C-Methyl-BAU | —OH | —H | —CH$_3$ | —H | —H | —H |
| m-Hydroxy-BAU | —OH | —H | —H | —H | —OH | —H |
| m-Methoxy-BAU | —OH | —H | —H | —H | —OCH$_3$ | —H |
| p-O-Isopropyl-BAU | —OH | —H | —H | —OCH(CH$_3$)$_2$ | —H | —H |
| N3-BB-BAU | —OH | —H | —H | —H | —H | -p-Benzyloxybenzyl |
| BBAU | —OH | —H | —H | —H | -Oxybenzyl | —H |
| succ-BBAU | —OCOCH$_2$CH$_2$COOH | —H | —H | —H | -Oxybenzyl | —H |
| HM-BBAU | —OH | —CH$_2$OH | —H | —H | -Oxybenzyl | —H |
| succ-HM-BBAU | —OCOCH$_2$CH$_2$COOH | —CH$_2$OH | —H | —H | -Oxybenzyl | —H |
| DA-BBAU | —NH$_2$ | —CH$_2$NH$_2$ | —H | —H | -Oxybenzyl | —H |
| AM-BBAU | —OH | —CH$_2$NH$_2$ | —H | —H | -Oxybenzyl | —H |
| C-Methyl-BBAU | —OH | —H | —CH$_3$ | —H | -Oxybenzyl | —H |
| BBBAU | —OH | —H | —H | —H | -Oxy(p-benzyloxy)benzyl | —H |

The molecular structures of exemplary uridine phosphorylase inhibitors are shown below:

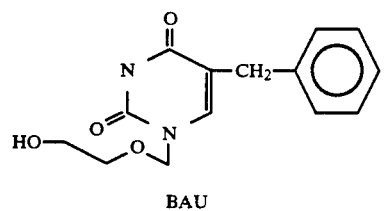

BAU

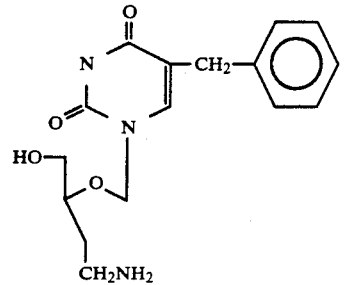

AM-BAU

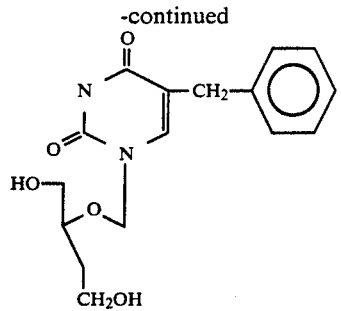

HM-BAU

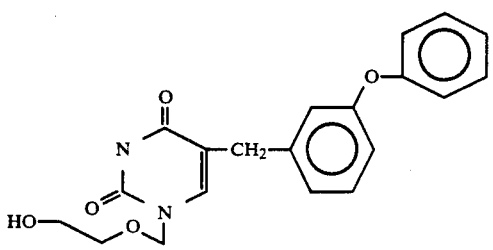

BBAU

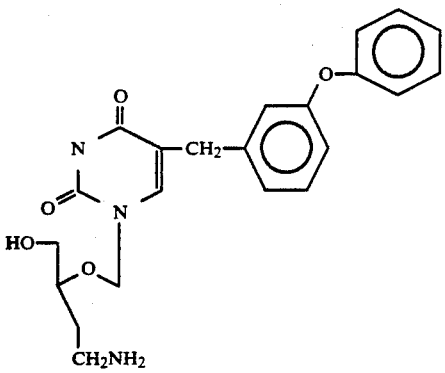

AM-BBAU

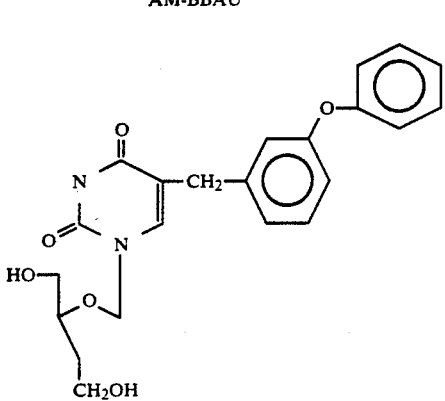

HM-BBAU

For further disclosures of uridine phosphorylase inhibitors and methods of synthesizing such compounds, see U.S. Pat. No. 4,613,604 issued to Chu et al. on Sept. 26, 1986; Niedzwicki et al., Vol 30 *Biochemical Pharmacology* pp. 2097-2101 (1981); Niedzwicki et al., Vol 31 *Bicchemical Pharmacology* pp. 1857-1861 (1982); and Lin et al., Vol 25 *J. Med Chem.* pp. 971-973 (1985)

Studies to date suggest that nucleoside analogue toxicity in bone marrow cells during the treatment of AIDS is due to their interference in the nucleotide metabolism of the bone marrow cells.

In vitro assays on bone marrow cells have revealed that the toxic effects of antiviral nucleoside analogues (i.e., 5 μM concentrations of AZT for 2 hours) can be essentially completely reversed with non-toxic concentrations of 50-100 μM of uridine (and also cytidine, probably through conversion to uridine by cytidine deaminase). Moreover, no impairment of suppression of viral replication (assessed by inhibition of reverse transcriptase) was detected with uridine even in the presence of combination molar ratios (uridine/AZT) as high as 10,000/1.

It also appears that administration of uridine phophorylase inhibitors can increase the in vivo plasma levels of uridine required to overcome nucleoside analogue toxicity without inconvenience and/or side effects of continuous infusion of high doses of uridine, itself, during therapy. Moreover, uridine phosphorylase inhibitors exhibit low toxicity; for example, BAU was nontoxic per se for human bone marrow cells and even at concentrations as high as 100μM, BAU had no substantial effect on human CFU-GM cell proliferation.

The pyrimidine nucleoside analogues of the present invention inhibit viral replication when administered in amounts ranging from about 10 mg to about 100 mg per kilogram of body weight per day depending upon the potency and toxicity of the particular analogue and such dosage units are employed so that a total of from about 0.7 to about 7 grams of the nucleoside analogue are administered for a subject of about 70 kg of body weight in a 24-hour Period. For example, one presently accepted protocol for AZT treatment calls for 200 mg every four hours. The uridine phosphorylase inhibitors protect or rescue the subject's bone marrow cells from nucleoside toxicity when administered in amounts ranging from about 50 mg to about 400 mg per kilogram of body weight per day again depending upon the potency and toxicity of the particular phophorylase, and such dosage units can be employed so that a total of from about 3.5 to about 28 grams of uridine phosphorylase inhibitor is administered for a subject of about 70 kg of body weight in a 24 hour period. Uridine, itself, can be administered to raise the subjects plasma uridine levels in amounts ranging from about 30 mg to about 250 mg per kilogram of body weight, preferably by intravenous injection on a periodic basis A plasma uridine level of from 10 μM to about 50 μM is preferred.

This dosage regimen of combination therapy may be adjusted to provide the optimum therapeutic response. For example, several divided doses may be administered daily or the dose may be proportionally reduced as indicated by the exigencies of the therapeutic situation. A decided practical advantage is that the active compounds may be administered in any convenient manner, such as by the oral, intravenous, intramuscular, or subcutaneous routes.

The active compounds may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions syrups, wafers, and the like. Such compositions and preparations should contain at least 0.1% of active compound The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: A binder, as gum tragacanth, acacia, cornstarch, or gelatin; excipients, such as dialcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compounds sucrose as a sweetening agent, methyl and propylparabens as preservatives, a dye and flavoring, such as cherry or orange flavor Of course, any material used in preparing any dosage unit form should be pharmaceutically pure and substantially non-toxic in the amounts employed In addition, the active compounds may be incorporated into sustained-release preparations and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It should be clear that various modifications, additions and subtractions can be made without departing from the spirit or scope of the invention. For example, it should be appreciated that the present invention can also be employed in conjunction with other chemotherapeutical or biological response-modifying agents. For example, the combination therapy of the present invention can be employed in tandem with the administration of bone marrow stimulating factors, such as granulocyte-macrophage colony stimulating factors (GM-CFSs), other colony stimulating factors, erythropoietin (EPO) and other materials which stimulate hematopoietic activity. (For a further discussion of GM-CSF activity, see Hammer et al., Vol. 31, *Antimicrobial Agents and Chemotherapy*, pp. 1046–1050 (1987).) Similarly, the combination therapy of the present invention can be undertaken in conjunction with efforts to stimulate the immune system, such as the administration of interferons (e.g., alpha-A interferon) or other lymphokines.

What is claimed is:

1. In a method of treating a subject infected with a retrovirus by administering a pyrimidine nucleoside compound in an amount effective to disrupt viral replication in infected cells, the improvement which comprises administering thereto a uridine phosphorylase inhibitor in an amount effective to decrease nucleoside toxicity in uninfected cells.

2. The method of claim 1 wherein the pyrimidine nucleoside compound is 3'-azido-3'deoxythymidine.

3. The method of claim 1 wherein the pyrimidine nucleoside compound is 3'-azido-2',3'-dideoxyuridine.

4. The method of claim 1 wherein the pyrimidine nucleoside compound is 2',3'-dideoxycytidin-2'-ene.

5. The method of claim 1 wherein the pyrimidine nucleoside compound is 3'-deoxy-3'-deoxythymidin-2'-ene.

6. The method of claim 1 wherein the uridine phosphorylase inhibitor is benzylacyclouridine,.

7. The method of claim 1 wherein the uridine phosphorylase inhibitor is benzyloxybenzylacyclouridine.

8. The method of claim 1 wherein the uridine phosphorylase inhibitor is aminomethyl-benzylacyclouridine.

9. The method of claim 1 wherein the uridine phosphorylase inhibitor is aminomethyl-benzyloxybenzylacyclouridine.

10. The method of claim 1 wherein the uridine phosphorylase inhibitor is hydroxymethyl-benzylacyclouridine.

11. The method of claim 1 wherein the uridine phosphorylase inhibitor is hydroxymethyl-benzyloxybenzylacyclouridine.

12. The method of claim 1 wherein the method further includes administering uridine to said subject in amount effective to raise the subject's plasma uridine levels.

13. In a pharmaceutical composition comprising a pyrimidine nucleoside compound in an amount effective to disrupt viral replication in retrovirus-infected cells and a pharmaceutically acceptable carrier, the improvement comprising a uridine phosphorylase inhibitor in an amount effective to decrease nucleoside toxicity in uninfected cells.

14. The pharmaceutical preparation of claim 13 wherein the pyrimidine nucleoside compound is 3'-azido-3'deoxythymidine.

15. The pharmaceutical preparation of claim 13 wherein the pyrimidine nucleoside compound is 3'-azido-2',3'-dideoxyuridine.

16. The pharmaceutical preparation of claim 13 wherein the pyrimidine nucleoside compound is 2',3'-dideoxycytidin-2'-ene.

17. The pharmaceutical preparation of claim 13 wherein the pyrimidine nucleoside compound is 3'-deoxy-3'-deoxythymidin-2'-ene.

18. The pharmaceutical preparation of claim 13 wherein the uridine phosphorylase inhibitor is benzylacyclouridine.

19. The pharmaceutical preparation of claim 13 wherein the uridine phosphorylase inhibitor is benzyloxybenzylacyclouridine.

20. The pharmaceutical preparation of claim 13 wherein the uridine phosphorylase inhibitor is aminomethyl-benzy lacyclouridine.

21. The pharmaceutical preparation of claim 13 wherein the uridine phosphorylase inhibitor is aminomethyl-benzyloxybenzylacyclouridine.

22. The pharmaceutical preparation of claim 13 wherein the uridine phosphorylase inhibitor is hydroxymethyl-benzylacyclouridine.

23. The pharmaceutical preparation of claim 13 wherein the uridine phosphorylase inhibitor is hydroxymethyl-benzyloxybenzylacyclouridine.

24. In a method of treating a retroviral infection by administering a pyrimidine nucleoside compound in a amount effective to disrupt viral replication in retrovirus-infected cells, the improvement comprising providing uninfected cells with an effective amount of uridine to reduce nucleoside toxicity in said uninfected cells.

25. The method of claim 24 wherein the improvement further comprises administering a uridine phosphorylase inhibitor in order to provide said effective amount of uridine.

26. A pharmaceutical composition comprising a therapeutically effective amount of 3'-azido-3'-azido-3'-deoxythymidine and a therapeutically effective amount of a compound which inhibits anemia by providing increased intracellular uridine levels in bone marrow progenitor cells in combination with a pharmaceutically acceptable carrier or diluent.

* * * * *

UNITED STATES PATENT AND TRADEMARK OFFICE
CERTIFICATE OF CORRECTION

PATENT NO. : 5,077,280

DATED : December 31, 1991

INVENTOR(S) : J-P. Sommadossi and M.H. el Kouni

It is certified that error appears in the above-identified patent and that said Letters Patent is hereby corrected as shown below:

Column 1, line 10, "infections" should read --infectious--;

Column 1, line 16, a period should follow "(HIV)";

Column 2, line 37, "issued to 071,680 issued to Cook" should read --issued to Verheyden et al. on June 18, 1974; U.S. Patent 4,071,680 issued to Cook--;

Column 5, line 40, "Bicchemical" should read --Biochemical--;

Column 6, line 7, "Period." should read --period.--;

Column 6, line 22, a period should follow "periodic basis";

Column 6, line 44, a period should follow "active compound";

Column 6, line 68, a period should follow "orange flavor";

UNITED STATES PATENT AND TRADEMARK OFFICE
CERTIFICATE OF CORRECTION

PATENT NO. : 5,077,280
DATED : December 31, 1991
INVENTOR(S) : J-P. Sommadossi and M.H. el Kouni It is certified that error appears in the above-indentified patent and that said Letters Patent is hereby corrected as shown below:

Column 7, line 3, a period should follow "employed";

Column 7, line 21, a period should follow "exists";

Column 7, line 28, a period should follow "vegetable oils"; and

Column 10, lines 16-17, "3'-azido-3'deoxythymidine" should read -- 3'-azido-3'deoxythymidine--.

Signed and Sealed this

Twelfth Day of April, 1994

Attest:

BRUCE LEHMAN

Attesting Officer

Commissioner of Patents and Trademarks